(12) United States Patent
Nguyen-Dinh et al.

(10) Patent No.: US 11,229,799 B2
(45) Date of Patent: Jan. 25, 2022

(54) SYSTEM FOR COUPLING A CARDIAC AUTONOMOUS CAPSULE TO A TOOL FOR IMPLANTING THE SAME

(71) Applicant: CAIRDAC, Antony (FR)

(72) Inventors: An Nguyen-Dinh, La Riche (FR); Willy Regnier, Longjumeau (FR)

(73) Assignee: CAIRDAC, Antony (FR)

( * ) Notice: Subject to any disclaimer, the term of this patent is extended or adjusted under 35 U.S.C. 154(b) by 175 days.

(21) Appl. No.: 16/655,198

(22) Filed: Oct. 16, 2019

(65) Prior Publication Data

US 2020/0164215 A1    May 28, 2020

(30) Foreign Application Priority Data

Oct. 17, 2018 (FR) ...................................... 1871199

(51) Int. Cl.
| | | |
|---|---|---|
| *A61N 1/375* | (2006.01) | |
| *A61N 1/372* | (2006.01) | |
| *A61N 1/05* | (2006.01) | |

(52) U.S. Cl.
CPC ......... *A61N 1/3756* (2013.01); *A61N 1/0573* (2013.01); *A61N 1/37205* (2013.01)

(58) Field of Classification Search
CPC . A61N 1/3756; A61N 1/0573; A61N 1/37205

USPC .......................................................... 607/36
See application file for complete search history.

(56) References Cited

U.S. PATENT DOCUMENTS

| | | |
|---|---|---|
| 8,340,780 B2 | 12/2012 | Hastings et al. |
| 9,993,648 B2 | 6/2018 | Kelly et al. |
| 2007/0135883 A1 | 6/2007 | Drasler et al. |
| 2009/0204170 A1* | 8/2009 | Hastings ............... A61N 1/3756 607/33 |
| 2011/0112548 A1 | 5/2011 | Fifer et al. |
| 2014/0046395 A1 | 2/2014 | Regnier et al. |
| 2014/0378991 A1* | 12/2014 | Ollivier .............. A61N 1/37205 606/129 |
| 2016/0213919 A1 | 7/2016 | Suwito et al. |
| 2016/0279423 A1* | 9/2016 | Kelly ..................... A61N 1/372 |
| 2017/0281261 A1* | 10/2017 | Shuros ................. A61B 18/148 |
| 2018/0028805 A1* | 2/2018 | Anderson ........... A61B 17/3468 |

* cited by examiner

*Primary Examiner* — Erin M Piateski
(74) *Attorney, Agent, or Firm* — Steven M. Greenberg, Esq.; Shutts & Bowen LLP

(57) ABSTRACT

A capsule includes a tubular body with, at its proximal end, a coupling member adapted to cooperate with a conjugated coupling member mounted at the distal end of a catheter of the implantation tool, for the transmission of a torque for the rotational driving of the capsule by the catheter. The coupling member of the tool includes a dihedral-shaped imprint, with two diverging arms in a V-arrangement, and the capsule coupling member includes a convex surface adapted to frictionally and slidingly urge against the diverging arms of the V-shape.

15 Claims, 5 Drawing Sheets

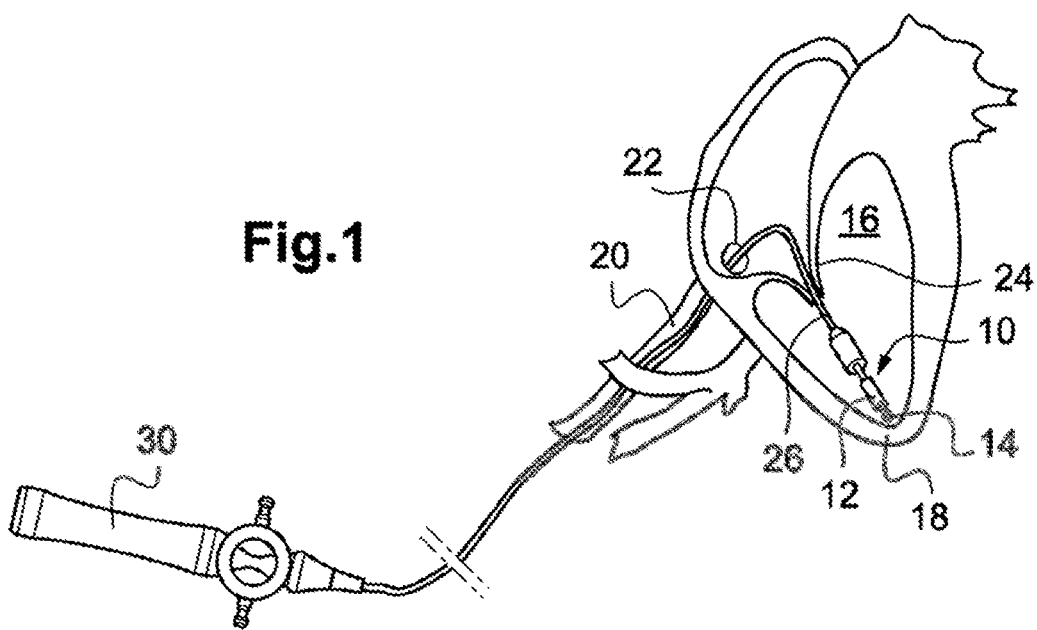
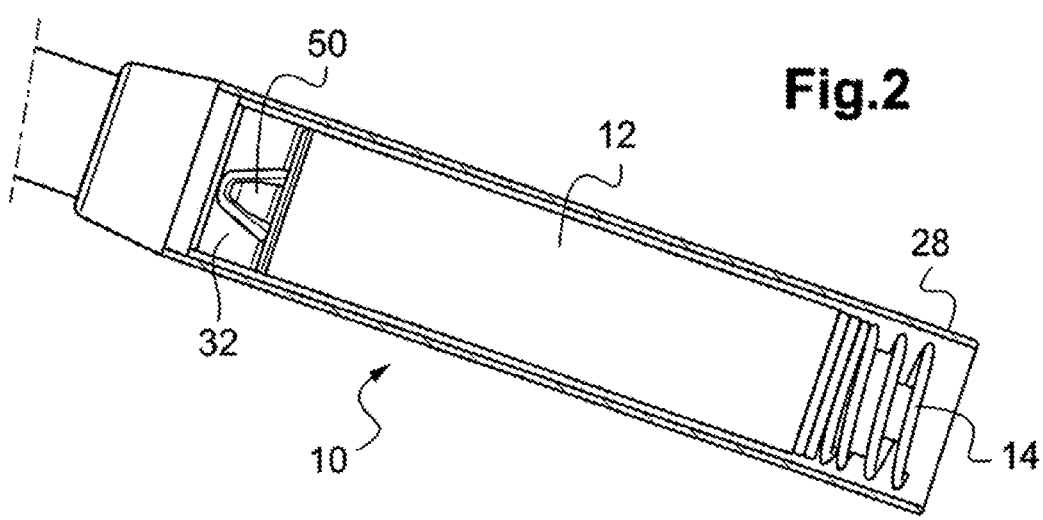

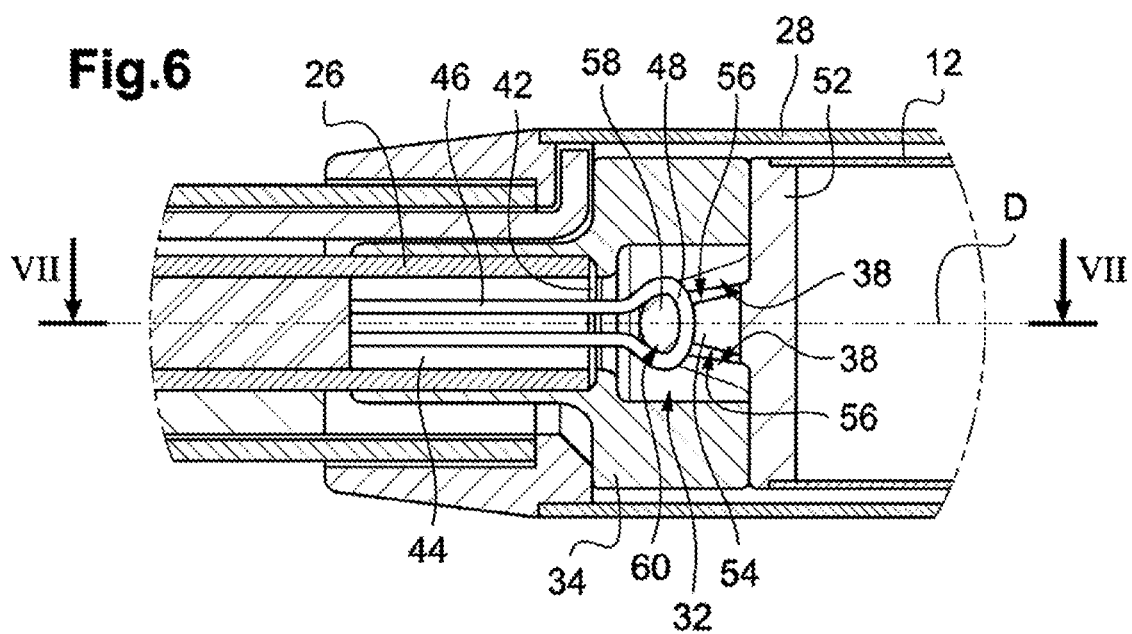
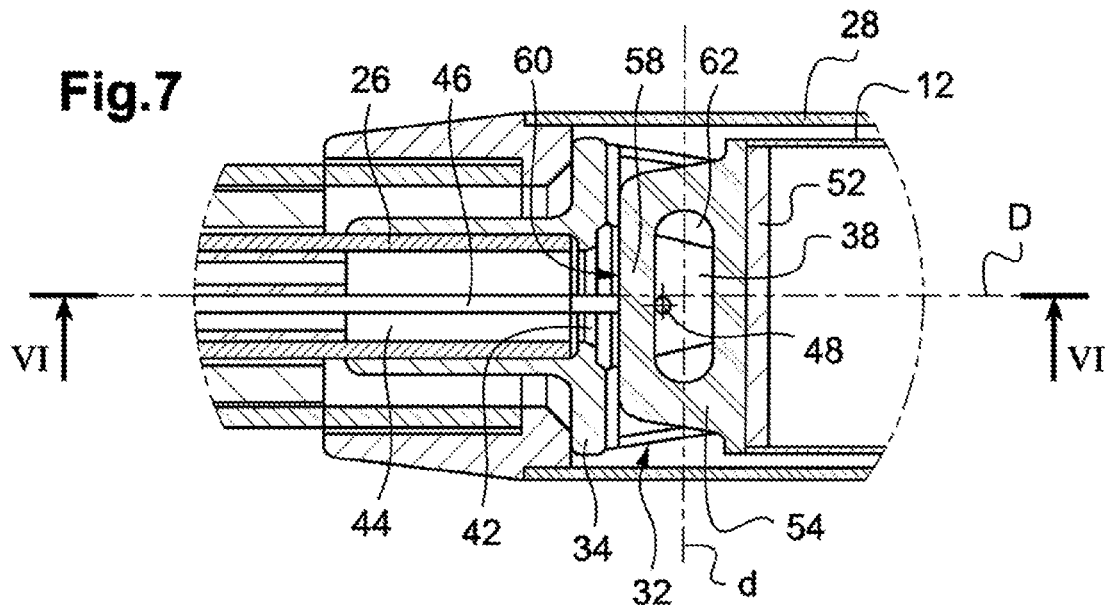

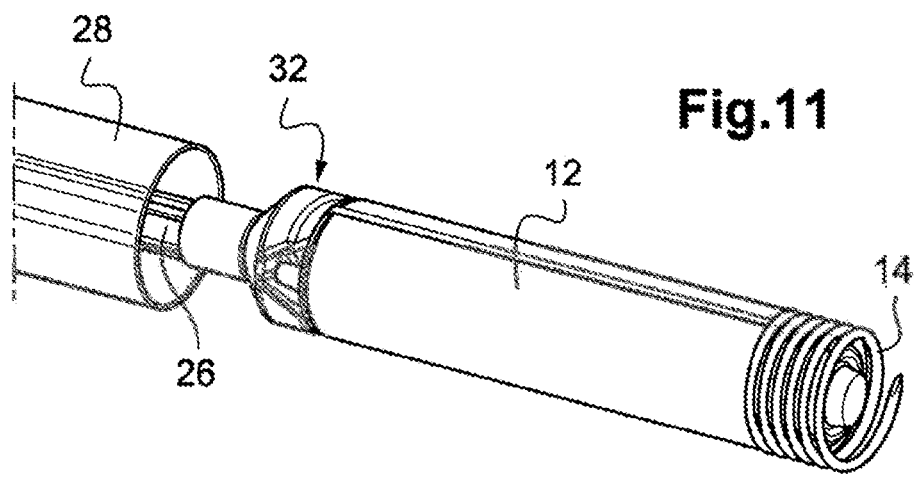
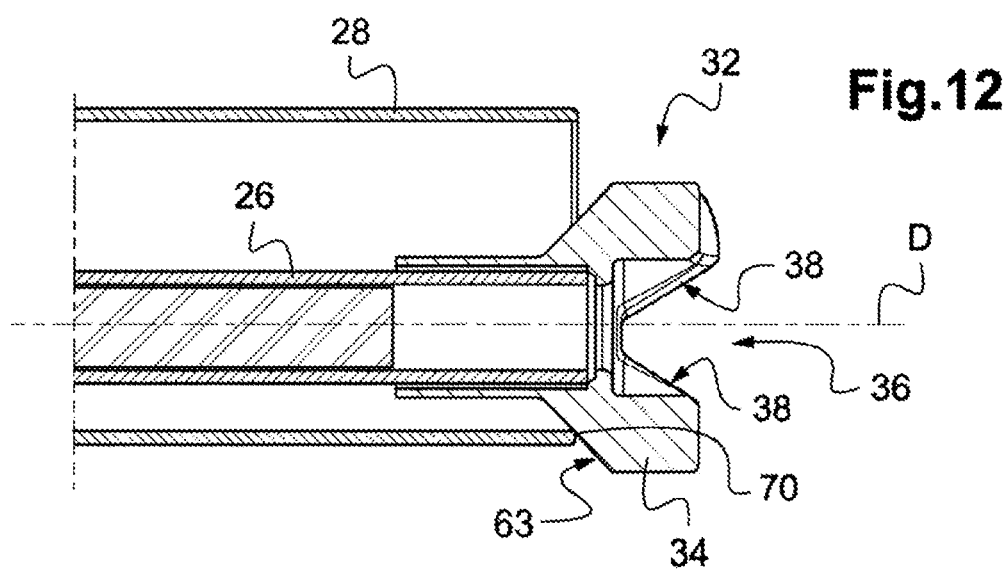

SYSTEM FOR COUPLING A CARDIAC AUTONOMOUS CAPSULE TO A TOOL FOR IMPLANTING THE SAME

CROSS REFERENCE TO RELATED APPLICATIONS

This application claims priority under 35 U.S.C. § 119(a) to French patent application number 18 71199, filed on Oct. 17, 2018, the entire teachings of which are incorporated herein by reference.

BACKGROUND OF THE INVENTION

Field of the Invention

The invention relates to implantable medical devices, in particular devices of the autonomous implantable capsule type. More particularly, the invention relates to such devices which are in the form of an autonomous capsule implanted in a heart chamber (ventricle, atrium or even arterial left heart chamber), hereinafter referred to as "autonomous capsule", "leadless capsule" or simply "capsule".

Description of the Related Art

Autonomous capsules are devoid of any physical connection to a main device, either an implanted device (such as a stimulation pulse generator casing) or a non-implanted device (external peripheral device such as a programmer or a monitoring device for remote follow-up of the patient). For that reason, autonomous capsules are referred to as "leadless" capsules, to distinguish these capsules from electrodes or sensors arranged at the distal end of a conventional lead, along the whole length of which run one or several conductors galvanically connecting the electrode or the sensor to a generator connected to an opposite, proximal end of the lead. In the case of cardiac application, the capsule continuously monitors the patient rhythm and if necessary delivers to the heart pacing, resynchronization and/or defibrillation electrical pulses in case of rhythm disorders detected by the capsule. The capsule may be an epicardic capsule fixed to the external wall of the heart, or an endocavitary capsule fixed to the internal wall of a ventricular or atrial chamber, or also a capsule fixed to a vessel wall near the myocardium. Several published patent applications, including US 2009/0171408 A1 (Solem), US 2017/0151429 A1 (Regnier) and WO 2018/122244 A1 (Regnier), describe various examples of such intracardiac leadless capsules. The capsules include various electronic circuits, sensors, etc., as well as wireless communication transmitter/receiver means for remote exchange of data, the whole being integrated in a body of very small size adapted to be implanted in sites of difficult access or leaving small room, such as the ventricle apex, the internal wall of the atrium, etc.

Of note, problems exist which are related to the implantation in situ of such capsules when these latter are not provided at their distal end with an anchoring member adapted to penetrate the tissues of a body wall at the chosen implantation site. A typical example of such an anchoring member includes a protruding helical screw axially extending the capsule body and intended to enter the heart tissue by being screwed thereinto at the implantation site. This anchoring mode is however not limitative of the invention, which may also apply to other types of anchoring members, implementing e.g. needles, hooks, barbs, etc. entering the tissues to permanently secure the medical device thereto.

In the case of endocavitary capsules (i.e. capsules to be fixed to the inner wall of a ventricular or atrial chamber, by opposition to epicardic capsules, fixed to the outer wall of the heart), the "delivery", i.e. the positioning at the implantation site, consists in mounting the capsule at the end of the guide catheter of an implantation accessory, then to make it move along the peripheral venous network up to the chosen site, for example the apex of the right ventricular chamber. Once the implantation site reached, the practitioner imparts to the capsule, through the guide catheter, combined movements of i) axial translation, to make the capsule move forward up to touch the heart wall and exert a pressure against the latter, and ii) rotation of the capsule about its axis, to screw the anchoring member into the thickness of the heart wall. Once the capsule firmly anchored in the wall of the heart, the operator proceeds to the "release" of the capsule, i.e. its separation from the implantation accessory, so that the capsule then become fully autonomous.

One of the difficulties is, at the time of fixing the capsule into the wall, to avoid any risk of "coring" the tissues due to an excessive screwing. For that purpose, it is imperative, at the time of screwing the anchoring member, not to exceed a limit torque (hereinafter "coring torque") beyond which the anchoring screw would be liable to locally tear the tissues under the effect of rotation of the screw without forward move of the latter, until causing a laceration of the tissues and, in the extreme, a perforation of the wall with a risk of tamponade (in particular, in case of implantation into a thin wall such as the interatrial septum or the apical area of the right ventricle).

So as to address the foregoing problems, one patent publication, WO 2017/202724 A1 (Ollivier), proposes a secure coupling solution combining specific capsule and implantation tool. This document describes means for the translational and rotational fastening of the implantation tool guide catheter distal end to the capsule proximal area (that which is opposed to the anchoring member). These means are disconnectable so that the capsule can be released once in position, and they include a simple disengageable mechanism making it possible, during the screwing of the anchoring member, to limit the torque applied to the capsule by the implantation tool.

This mechanism consists of a helical spring used in radial compression (i.e. for its constriction effect). This spring is mounted at the distal end of the guide catheter and rolled around a docking pin of the capsule, extending the latter on the proximal side thereof. The spring then plays a double role of (disengageable) connection means and of torque limiter against an excessive screwing action that could lead to a coring of the tissues. Indeed, at the end of screwing, when the capsule body comes against the wall, the additional torque due to the reaction of the screw is absorbed by the connection between the spring and the capsule docking pin: the practitioner can hence continue without risk to rotate the guide catheter beyond what is strictly necessary for a complete screwing of the capsule into the wall.

A drawback of this known technique is the necessity to provide at the proximal portion of the capsule (i.e. on the side which is opposed to the anchoring screw) a docking pin that is long enough so that the implantation tool spring can catch it. This requirement necessarily increases the overall length of the capsule, which goes against the requirements of extreme miniaturization imposed to the leadless capsules. An increased length moreover makes it more difficult to move the capsule forward along the peripheral venous network up to the chosen site.

Another drawback of this known technique is the difficulty that may occur if, after implantation and release of the capsule, the practitioner notices, on the basis of the electric tests, that the implantation site is not optimum and wants to explant the capsule to reimplant it at a nearby site, or if he wants to definitively explant an already-positioned capsule. He will hence have to operate the implantation tool (which had been disconnected from the capsule) so as to place again the helical spring against the docking pin of the capsule and to try, by combined pushing and rotational moves of the catheter, to put this spring back about the pin so as to be able to exert again on the latter the radial clamping effort required to couple the catheter to the capsule. These operations are extremely tricky, or even impracticable in real operating conditions, which constitute a serious limitation to the possibilities of use of this known system.

Other solutions for coupling a leadless capsule to a specific implantation tool have been proposed, but none of them provide a dual functionality i) of intrinsic limitation of the rotation torque exerted on the capsule by the tool at the time of implantation and ii) of reversibility to allow an easy explantation, a fortiori thanks to a mechanical structure that is simple, reliable, and of easy and inexpensive industrialization.

Hence, while contemporary patent publications describe an implantable capsule provided, at its rear (proximal) end, with a "retainer pin" or "retainer shaft" directed transversally (i.e. radially) with respect to the capsule body. The implantation tool includes, at its front (distal) end, two protruding fingers approximately planar and parallel, directed axially towards the rear of the capsule and catching between each other the transversal retainer pin of the latter. One of the fingers has a rounded hollow imprint receiving the pin introduced between the two fingers. To lock the pin in position in the space formed between the two fingers, a wire is forcibly interposed between the free side of the pin and the opposite finger. To release the capsule once the latter in position, the wire ("locking pull-wire") is removed, which relieves the pressure on the pin and releases the latter from the space in which it was located between the fingers, which has for consequence to uncouple the capsule from the implantation tool.

In a variant described in the publication WO 2007/067231 A1, the pin is clamped between the fingers only under the effect of the proper elasticity of these latter. The release of the capsule is then performed by pushing on a "push-wire" that expels the pin out of the space between the fingers. The mechanism described by these two documents generates, by nature, no intrinsic limitation of the rotation torque exerted on the capsule by the tool. It is not either directly or simple reversible. As well, the capsule described in publication US 2016/213919 includes a mushroom or hook-shaped rear end, intended to facilitate explantation by means of a "lasso" hooking this rear end so as to then be able to guide and approach a catheter up to the capsule from the outside. This particular shape provides no torque limitation nor reversibility in the above-mentioned sense.

The implantation tool described in publication US 2018/028805 has a coupling member in the form of flexible claws gripping and catching the mushroom-shaped rear end of the capsule. This system ensures an intrinsic function of limitation of the rotation torque, insofar as the fingers will turn freely when the capsule will oppose a certain resistance to the rotation. To detach the capsule from the tool claws, it is necessary to provide an additional mechanism because the capsule/tool uncoupling is not automatic; a shaft of the catheter must be introduced into the central lumen and operated to axially push back the rear end of the capsule and to release the latter from the claws by an elastic deformation of these latter. Besides its structural complexity, this mechanism provides no reversibility, the explantation requiring the implementation of a technique such as that described by above-mentioned US 2016/213919 A1.

Finally, the publication U.S. Pat. No. 9,993,648 describes a structure of implantation tool with a tube provided at its distal end with an approximatively conical, funnel shape, in which is received the mushroom-shaped rear end of the capsule. Two slots arranged in the funnel provide the latter with a certain radial elasticity that allows it to clamp the rear end of the capsule when the latter is forcibly inserted into the bottom of the funnel. This tool/capsule coupling mode is theoretically reversible, but such an operation would be in practice very difficult to contemplate due to the absence of mutual pre-guiding and pre-centering of the capsule and the tool head so that the two shapes can fit into each other. In particular, the planar front face of the tool head is liable to create a blocking situation if the capsule axis and the tool axis are not aligned with each other when these two elements are moved closer to each other. Now, an alignment, even approximative, of these two axes is in practice not unthinkable in the real conditions of a surgical operation, in which the free, rear end of the capsule permanently oscillates following the heart beats and the turbulences of the surrounding blood flow.

BRIEF SUMMARY OF THE INVENTION

One of the objects of the invention is to propose a system for coupling an autonomous capsule to its implantation tool that is easy to implement and of simple structure, while integrating a torque limiting mechanism providing during the implantation an absolute safety against any risk of coring and laceration of the tissues due to an excessive screwing of the capsule into the wall. Another object of the invention is to propose such a coupling system that is fully reversible, i.e. with which, after a first uncoupling, the implantation tool can be simply, safely and rapidly coupled again to the capsule, so as to allow this capsule to be unscrewed to be reimplanted at another site (or definitively explanted). Still another object of the invention is to propose such a capsule which manufacturing cost is reduced, thanks in particular to a reduced number of simple-shape parts and thanks to the use of technologies and components that have been tested in similar applications.

For that purpose, the invention proposes a unit including, in a manner known per se: an autonomous implantable capsule including a tubular body provided at its distal end with an anchoring member adapted to enter a tissue of an organ wall, and at its proximal end with a coupling member adapted to cooperate with a conjugated coupling member of the tool; and a tool for guiding and anchoring the capsule to an implantation site including a catheter provided at its distal end with the conjugated coupling member. The coupling member of the capsule and the conjugated coupling member of the tool have complementary respective shapes adapted to allow the transmission of a torque rotationally driving the capsule by the catheter. The unit further includes a junction means adapted to selectively produce in the axial direction an effort for mutually moving closer and urging the coupling member of the capsule against the conjugated coupling member of the tool, for making the capsule rotationally and translationally integral with the catheter, then uncoupling the capsule from the catheter by relieving the effort.

Characteristically of the invention, the shape of the conjugated coupling member of the tool includes on the distal side in axial cross-section a V shape including two diverging arms, and the shape of the coupling member of the capsule includes at its proximal end a convex surface adapted to frictionally and slidingly urging against the diverging arms of the V-shape.

According to various advantageous subsidiary characteristics:

the V-shape is a dihedral shape with two diverging arms extending in respective planes, in particular with the line of intersection of the dihedron extending radially and/or with an angle of the dihedron included between 10¬∞ and 80¬∞, preferably included between 30¬∞ and 60¬∞;

the conjugated coupling member of the tool includes on the distal side a front surface adapted to urge against the proximal end of the capsule and including two front half-faces radially extending each respective diverging arm of the V-shape. The two front half-faces may advantageously extend in respective planes inclined in opposite directions with respect to a radial plane, wherein such planes can form in particular an angle of inclination with respect to the radial plane included between 5¬∞ and 15¬∞;

the tool conjugated coupling member is connected, on the proximal side, to the catheter by a flared connection portion which size in radial cross-section increases progressively from the catheter towards the conjugated coupling member;

the convex surface of the capsule coupling member is a cylindrical surface which axis is oriented radially;

the material of the capsule coupling member is a metallic material and the material of the tool conjugated coupling member is a polymer plastic material;

the material of the coupling member of the capsule, the material of the conjugated coupling member of the tool, the shape of the coupling member of the capsule and the shape of the conjugated coupling member of the tool are jointly chosen for producing, at the interface of contact between the shape of the capsule coupling member and the shape of the tool conjugated coupling member, a sufficient frictional contact force to: couple the capsule to the catheter and allow rotational driving the capsule by the catheter as long as a reaction torque exerted by the capsule anchoring member is lower than a predetermined threshold torque; and uncouple the capsule from the catheter as soon as the reaction torque exceeds the predetermined threshold torque, and hence interrupt the transmission to the capsule of the rotational driving torque;

the predetermined threshold torque is lower than 5 N·cm;

the junction means includes a retainer wire housed in a lumen of the catheter and exiting at the distal end of the catheter, and the retainer wire is fastened to the capsule coupling member, so that an axial traction exerted in proximal direction on the retainer wire pushes the capsule coupling member closer against the tool conjugated coupling member;

the tool further includes a tubular protective sleeve carried by the catheter distal end and defining an inner volume capable of housing, with an axial sliding degree of freedom: at least the proximal region of the capsule tubular body including the capsule coupling member; the tool conjugated coupling member; and the junction means.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 1 is an overall view illustrating the tool and the capsule of the invention, in situation during an operation of implantation into the right ventricle of the myocardium.

FIG. 2 illustrates the capsule of the invention coupled to the catheter inside the protective sleeve, before extension and screwing of the capsule.

FIG. 6 is an axial cross-section, along line VI-VI in FIG. 7, of the catheter docking part and of the capsule rear portion, coupled together.

FIG. 7 is an axial cross-section, along line VII-VII in FIG. 8, of the catheter docking part and of the capsule rear portion, coupled together.

FIG. 11 illustrates in perspective the capsule coupled to the catheter docking part, the unit being extended out of the tubular protective sleeve in a situation corresponding typically to a phase of recatching the capsule for explantation thereof.

FIG. 12 is an axial cross-section of the docking part and the distal end of the protective sleeve in the configuration of FIG. 11, illustrating in particular the role played during this operation by the insertion cone formed at the rear of the docking part.

DETAILED DESCRIPTION OF THE INVENTION

Figure 3:
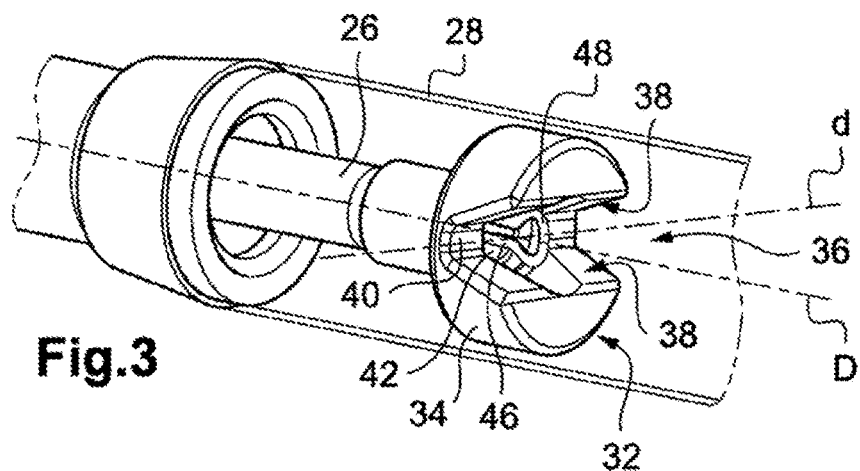
FIG. 3 is a perspective enlarged view of the catheter end with its docking part and the safety wire, inside the protective sleeve.

An exemplary embodiment of the invention will now be described with reference to the drawings.

FIG. 1 illustrates an implantation tool and an autonomous leadless capsule according to the invention, in situation during an operation of positioning this capsule in the right ventricle of a myocardium.

The capsule, denoted 10 (and represented in more detail in FIG. 2), includes, in a manner known per se, a tubular body 12 provided at one of its ends with a protruding helical anchoring screw 14 axially extending the tubular body 12 and rotationally integral with the latter. The anchoring screw includes, in its distal portion, a length of the order of 1.5 to 2 mm of non-contiguous turns, intended to enter the heart tissue for securing the capsule thereto.

In the illustrated example, the capsule is implanted into the right ventricle 16 of a heart, in the bottom of this ventricle in the region of the apex 18. Access to the right ventricle 16 is made through the vena cava 20, via the sinus 22, then the tricuspid valve 24.

The implantation tool includes for that purpose a catheter 26 with, at its distal end, a tubular protective sleeve 28 housing the capsule, the latter being progressively extended out of the sleeve up to be docked to the heart wall. At the opposite, proximal end, the catheter 26 is connected to an operating handle 30 operated by the practitioner.

Here and hereinafter, the term "proximal" (or "rear") will be considered with respect to the implantation tool, i.e. towards the handle operated by the practitioner; likewise, the term "distal" (or "front") will refer to an opposite direction, hence close to the implantation site and to the anchoring screw 14 of the capsule. In the different figures appended, these proximal and distal directions correspond to the left and the right, respectively. Likewise, the term "axial" will be used with reference to the axis of the capsule, i.e. the greatest dimension thereof, herein the axis D of the cylindrical body 12, a "radial" direction being a direction located in a plane perpendicular to the axial direction.

Using various levers and buttons, the practitioner steers the catheter and makes it progress along the vena cava 20, then accurately steers the distal end up to the docking to the bottom of the ventricle 16. He hence imparts to the catheter 26, from the handle, a double movement of translation to press the distal end of the capsule against the wall, and of rotation to screw the capsule in order to anchor the latter into the wall.

FIG. 2 shows in a more enlarged view the capsule 10 with its tubular body 12 housed inside the protective sleeve 28, in a so-called "retracted position" configuration, in which the sleeve 28 covers the capsule, and in particular the anchoring screw 14, during the progression in the venous network, during the passage through the valve, etc. The sleeve 28 also protects the surrounding tissues from the potential risks of tearing by the screw before the latter reaches its definitive position.

Once the capsule has touched the implantation site, the practitioner operates a translation of the capsule in the distal direction, which has for effect to extend the latter out of the tubular protective sleeve 28 (in a configuration such as that illustrated in FIG. 11). By an axial rotation movement, he then screws the capsule into the heart wall until the front face of the tubular body 12, which carries an electrode (not shown), urges against the wall. In this position, which is the definitive position of the capsule, the practitioner can then uncouple the delivery catheter from the capsule, then proceed to the removal of the guide catheter out of the organism by the reverse operation to that which had been implemented for the implantation.

The invention more particularly relates to the way to couple the capsule 10 to the catheter 26, by a means allowing the transmission of the rotation torque from the proximal end of the catheter, at the operation handle 30, to the distal end of the capsule 10 carrying the anchoring screw 14.

Characteristically, this means implements a system for transmitting and limiting the torque applied to the capsule by the catheter (and hence the torque exerted by the anchoring screw 14 on the heart tissues), which: i) guarantees a complete screwing of the capsule into the heart tissues at the implantation site; ii) avoids any coring of the heart wall; and iii) allows the practitioner, in case of difficulty, to recover the capsule after the latter has been released, in particular by reversibility of the coupling.

Figure 4:
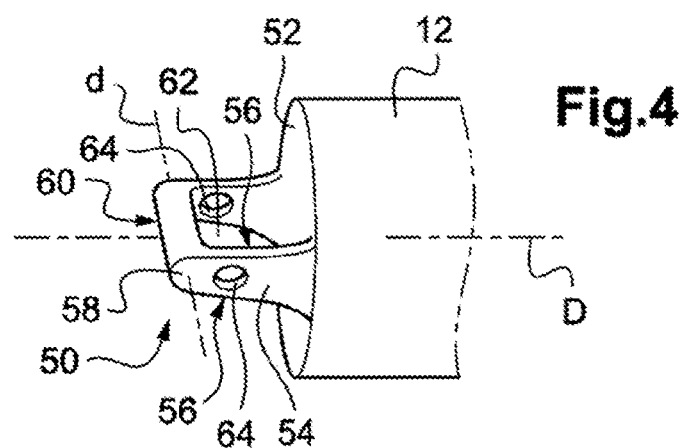
FIG. 4 is a perspective view showing, in isolation, the rear (proximal) portion of the capsule, with the conjugated shape intended for the coupling with the catheter docking part.
Figure 5:
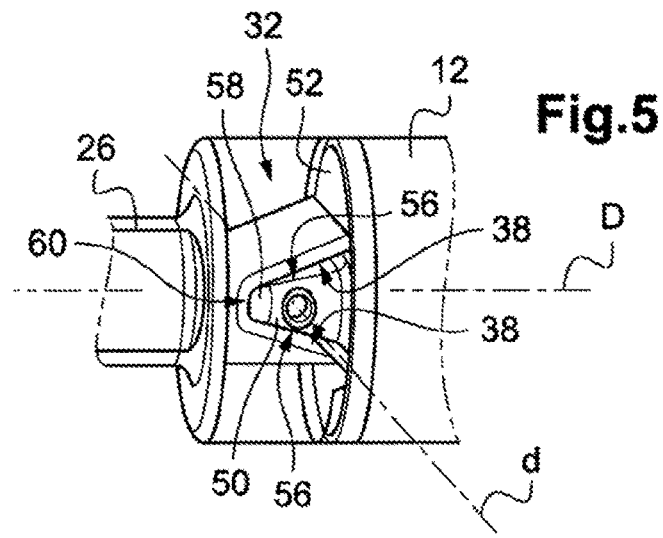
FIG. 5 illustrates in perspective the catheter docking part and the capsule conjugated shape, coupled together to allow the rotational and translational driving of the capsule by the implantation tool.

FIGS. 3 to 7 illustrate an embodiment of this coupling means according to the invention.

The distal end of the catheter 26 is provided with a coupling member 32, hereinafter called "docking part", cooperating with a conjugated coupling member 50 at the proximal portion of the body of the capsule 10, the portion being hereinafter called "rear of the capsule".

The docking part 32 has a cylindrical body 34 which diameter allows it to enter and slide into the tubular protective sleeve 28. This cylindrical body is advantageously made of a plastic material, such as a polymer of the PET (polyethylene terephthalate) or PEEK (polyetheretherketone) type or another injectable plastic material, possibly coated with a film of parylene (poly(p-xylylene) polymer), a material known for its hydrophobic and low friction coefficient properties. As a variant, it may also be made of a metallic material, such as stainless steel (for example, 316L), titanium or tantalum, with or without a coating for improving the friction coefficient.

On the distal side, the cylindrical body 34 includes an imprint consisted of a symmetrical, approximately V-shaped recess 36, with two inclined faces 38 extending along planes located on either side of the central axis D, with a symmetrical dihedral configuration, the axis d of this dihedron extending in a radial direction. The inclination of the faces 38 with respect to the axis D is chosen so that these faces form between each other an angle included between 10° and 80°, preferably from 30° to 60°, more precisely of 45° in the example illustrated in FIGS. 3 to 7.

The bottom 40 of the recess 36 has, at the place where the inclined faces 38 connect to each other, a rounded shape, cylindrical of revolution in the example illustrated.

The cylindrical body 34 is axially passed through by an axial orifice 42 opening into an inner lumen 44 of the catheter 26. This orifice 42 allows the passage of a safety wire 46 running through the whole length of the catheter 26 up to the operating handle at the proximal end; the safety wire 46 forms at the distal end a loop 48 extending approximately in the space defined between the inclined faces 38 of the recess 36.

The recess 36 of the docking part 32 is turned towards the rear 50 of the capsule, which is consisted of a conjugated coupling member liable to cooperate with the recess 36.

More precisely, the cylindrical body 12 of the capsule is closed on the rear by a lid 52 carrying a protrusion 54 which shape and size allow it to enter inside the opposite recess 36. The material of this protrusion 54 may be the same as that of the closing lid 52 and of the tubular body 12, i.e. a metallic material such as titanium, stainless steel (for example, 316L), tantalum, or a nickel-titanium alloy of the nitinol type, possibly with a coating to improve the friction coefficient. As a variant, it may also be made of a material such as a polymer of the PET or PEEK type.

The protrusion 54 includes two surfaces 56 symmetrical with respect to the axis D and forming together a ruled surface with two inclined flats 56 which size decreases towards the rear. The two flats 56 hence form approximately a V, which opening angle is lower than that of the V of the docking part 32 defined between the two inclined faces 38. At its proximal end 58, the protrusion 54 has a rounded surface 60, for example a surface that is cylindrical of revolution of axis d extending in a radial plane perpendicular to the main axis D. The radius of curvature of the rounded surface 60 is lower than that of the cylindrical surface 40 of the opposite docking part 32, so that the protrusion 54 can enter the recess 36 of the docking part up to the bottom of the latter.

Finally, the protrusion 54 includes a recess 62 allowing the passage of the loop 48 of the safety wire 46 (as illustrated in particular in FIGS. 6 and 7) and hence the fastening of the capsule body to this safety wire. As a variant, the protrusion 54 may include orifices such as 64 (see FIG. 4) formed in directions parallel to the transverse axis d and allowing the threading of the safety wire.

A first function of the unit consisted of the docking part 32 and of the conjugated coupling member 50 at the rear of the capsule is to ensure a pre-guiding between the body of the capsule 12, at its proximal end, with the end of the catheter 26 when the capsule is moved closer to its implantation tool by tensioning of the safety wire 46: this pre-guiding is ensured by the V-shape of the recess 36 and the protruding shape of the opposite protrusion 54, with a progressive reduction of the guiding clearance between the docking part 32 and the rear end of the capsule as these latter move closer to each other during the insertion into the tubular protective sleeve 28.

A second function of the unit consisted by the docking part 32 and the conjugated coupling member 50 is to ensure a limitation of the rotation torque transmitted to the capsule by the catheter via the tubular sleeve 28.

Firstly, once the rear of the capsule and the tubular sleeve have been coupled together by being moved closer to each other and by the safety wire 46 being tensioned, the protrusion 54 is pressed against the bottom of the recess 36 so that a translation applied to the catheter 26 and transmitted to the capsule by the tubular sleeve 28 extends the capsule out of the tubular protective sleeve 28 and makes it come into contact with the heart wall.

The practitioner can then begin to screw the capsule into the heart wall by imparting an axial rotation move to the catheter 26. Due to the contact between, on the one hand, the inclined faces 38 of the docking part 32 and, on the other hand, the opposite surface 56 of the protrusion 54, the rotation torque is transmitted to the capsule.

At the end of the screwing, the front face of the capsule that touches the surface of the heart wall exerts on the anchoring screw an axial reaction force that would be liable to produce a coring. But, as the above-mentioned contact between the inclined faces 38 and the opposite surface 56 is a friction contact (friction of the cylindrical surface 60 to the inclined plane of the faces 38), due to the reaction torque that increases relatively suddenly, the friction limit is rapidly reached and the docking part 32 exits from the protrusion 54, comparably to a screwdriver blade that escapes from the imprint of a screw head when the screw is blocked. The desired function of torque limitation and unclutching between the capsule and the catheter docking part is hence obtained.

The rotation torque beyond which this phenomenon occurs may be adjusted by a particular choice of: i) the respective materials of the docking part 32 and of the rear 50 of the capsule (a material choice that gives a metal-to-polymer friction contact in the described example); ii) the opening angle of the imprint formed by the recess 36, essentially the V angle of the inclined faces 38; and iii) the shape of the protrusion 54, and in particular the end 58 thereof (cylindrical shape 60 in the illustrated example).

It will be noted that, as regards the contact between the docking part 32 and rear 50 of the capsule, respectively, the invention is not limited to a metal/polymer friction contact (as in the illustrated example), but may be applied as well to a friction contact of the polymer/metal, metal/metal or polymer/polymer type, with the materials indicated hereinabove by way of example.

The limit torque beyond which the docking part 32 and the rear 50 of the capsule disconnect from each other is chosen lower than the coring limit (limit beyond which the anchoring screw would risk to locally tear the tissues under the effect of rotation of the screw without moving forward of the latter), while being sufficient to allow the penetration of the anchoring screw up to the complete screwing (tissue in contact with the front face of the capsule). A suitable value of the limit torque is typically lower than 5 N·cm.

Figure 8:
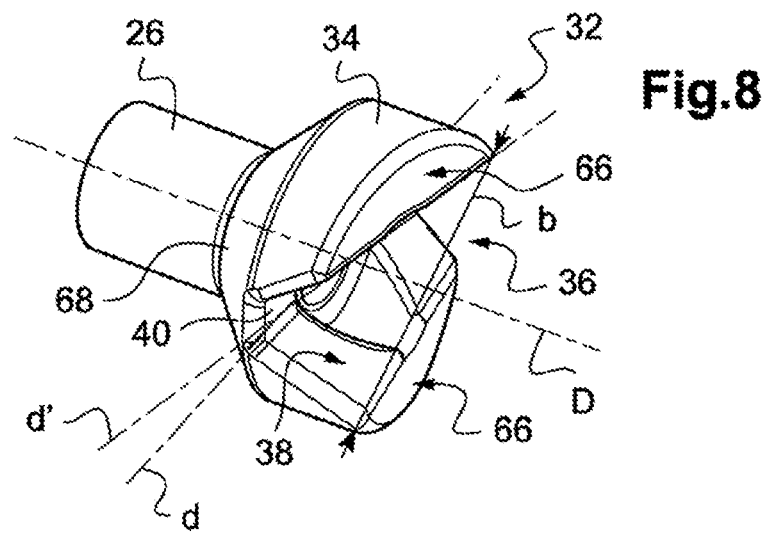
FIG. 8 illustrates in perspective, in isolation, a variant of the docking part of the previous figures.
Figure 9:
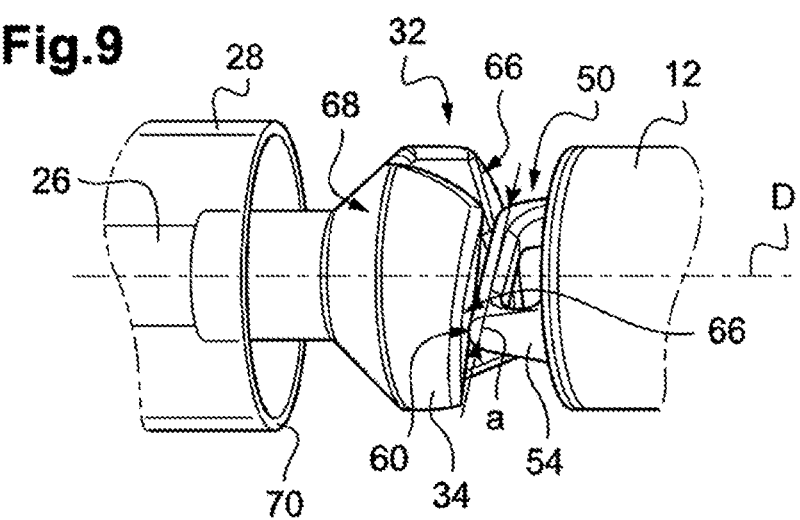
FIG. 9 illustrates in perspective the docking part of FIG. 8 and the capsule rear portion, at the time of docking between these two elements, just before the coupling thereof.
Figure 10:
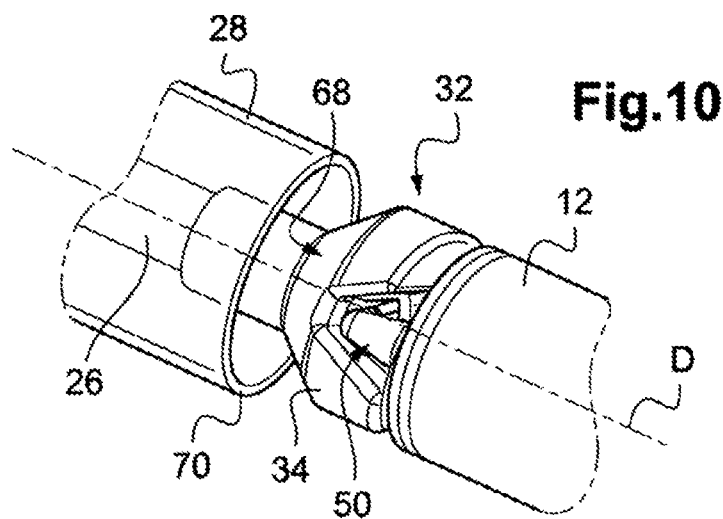
FIG. 10 illustrates in perspective the docking part and the capsule rear portion illustrated in FIG. 9, coupled together.

FIGS. 8 to 12 illustrate an advanced variant of the docking part 32.

In this variant, the docking part 32 includes a front surface turned towards the capsule consisted of two front half-faces 66 that extend radially each respective inclined face 38 of the recess 36. Unlike the embodiment of FIGS. 3 to 7, in which these half-faces were coplanar and extended in a radial plane, in this variant of FIGS. 8 to 12, the front half-faces 66 are inclined in opposite directions with respect to a radial plane (plane containing a radial axis d along which extends the bottom 40 of the recess 36). The inclination angle of the front half-faces 66 with respect to a radial plane, i.e. the angle between the directions d' and d in FIG. 8) is included between 5° and 15°, in one direction for one of the front half-faces and in the opposite direction for the other front half-face.

Due to the inclination of the front half-faces 66, during the docking of the capsule against the docking part 32, there is no longer stable position and the capsule is automatically directed towards the bottom of the imprint of the recess 36.

This characteristic is particularly advantageous when, after having implanted the capsule and uncoupled the latter from the tool, then after a first unfavorable electrical test, the practitioner wants to couple again the tool to the capsule, typically to unscrew the latter and screw it again at a nearby implantation site, estimated as being better.

Firstly, due to the reversible character of the just-described mechanism, a rotation torque exerted in a reverse direction on the docking part 32 will be transmitted to the tubular body 12 and hence to the helical screw 14, which allows unscrewing the capsule and hence detaching it progressively from the heart wall.

It will then be easy to move the docking part 32 closer to the rear 50 of the capsule by a traction on the safety wire. At the time when the rear 50 of the capsule comes into contact with the docking part 32, the configuration is that of FIG. 9, with the end surface 60 of the protrusion 54 urging against the front half-faces 66. To avoid any risk of blocking, and to be certain that the rear 50 of the capsule will always be in contact with at least one of the inclined half-faces 66, the axial length a (FIG. 9) of the protrusion 54 is chosen higher than the greatest dimension b (FIG. 8) between the connection apices located at the diametrically opposed, upper ends of the respective front half-faces. By continuing to pull on the safety wire, the end surface 60 slides along the inclined front half-faces 66 until entering the recess 36, coupling again the capsule to the docking part 32, with a configuration such as that illustrated in FIGS. 10 and 11.

It will be noted that these operations are made with the docking part and the capsule fully out of the protective sleeve 28. That way, the diameter of the catheter 26 being lower than the inner diameter of the tubular protective sleeve 28, during the operation, a misalignment of the axes may occur, as illustrated in FIG. 12. To facilitate the insertion of the docking part 32 and the reintroduction of the capsule into the tubular protective sleeve 28, the docking part 32 is advantageously connected to the distal end of the catheter 26 by an approximately conical portion 68, which hence comes into abutment against the edge 70 of the distal end of the catheter 26. The insertion cone of the connection portion 68 allows reducing progressively the misalignment, up to the complete realignment of the docking part 32 when the latter begins to enter the tubular protective sleeve 28.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

The invention claimed is:

1. A unit comprising an autonomous implantable capsule and a tool for guiding and anchoring the capsule to an implantation site, wherein:
   the capsule comprises a tubular body provided at its distal end with an anchoring member adapted to enter a tissue of an organ wall, and at its proximal end with a coupling member adapted to cooperate with a conjugated coupling member of the tool;
   the tool comprises a catheter provided at its distal end with said conjugated coupling member;
   the coupling member of the capsule and the conjugated coupling member of the tool having complementary respective shapes adapted to allow the transmission of a torque rotationally driving the capsule by the catheter;
   the unit further comprising a junction means adapted to selectively produce in the axial direction an effort for mutually moving closer and urging the coupling member of the capsule against the conjugated coupling member of the tool, for making the capsule rotationally and translationally integral with the catheter, then uncoupling the capsule from the catheter by relieving said effort,
   and wherein, further:
   the shape of the conjugated coupling member of the tool comprises on the distal side in axial cross-section, a recess turned towards the rear of the capsule, having a V-shape comprising two diverging inclined faces, and
   the shape of the coupling member of the capsule comprises at its proximal end a convex surface adapted to frictionally and slidingly urge against the diverging inclined faces of the V-shape.

2. The unit of claim 1, wherein the V-shape is a dihedral shape with two diverging inclined faces extending in respective planes.

3. The unit of claim 2, wherein the line of intersection of the dihedron extends radially.

4. The unit of claim 2, wherein the angle of the dihedron is comprised between 10° and 80°.

5. The unit of claim 4, wherein the angle of the dihedron is comprised between 30° and 60°.

6. The unit of claim 1, wherein the conjugated coupling member of the tool comprises on the distal side a front surface adapted to urge against the proximal end of the capsule and comprising two front half-faces radially extending each respective one of the diverging inclined faces of the V-shape.

7. The unit of claim 6, wherein the two front half-faces extend in respective planes inclined in opposite directions with respect to a radial plane.

8. The unit of claim 7, wherein the angle of inclination of the planes of the respective front half-faces with respect to the radial plane is comprised between 5° and 15°.

9. The unit of claim 1, wherein the conjugated coupling member of the tool is connected on the proximal side to the catheter by a flared connection portion which size in radial cross-section increases progressively from the catheter towards the conjugated coupling member.

10. The unit of claim 1, wherein the convex surface (60) of the capsule coupling member is a cylindrical surface which axis (d) is oriented radially.

11. The unit of claim 1, wherein the material of the capsule coupling member is a metallic material and the material of the tool conjugated coupling member is a polymer plastic material.

12. The unit of claim 1, wherein:
   the material of the coupling member of the capsule, the material of the conjugated coupling member of the tool, the shape of the coupling member of the capsule, and the shape of the conjugated coupling member of the tool are jointly chosen for producing, at the interface of contact between the shape of the coupling member of the capsule and the shape of the tool conjugated coupling member, a frictional contact force sufficient to:
   couple the capsule to the catheter and allow rotational driving the capsule by the catheter as long as a reaction torque exerted by the capsule anchoring member is lower than a predetermined threshold torque; and
   uncouple the capsule from the catheter as soon as the reaction torque exceeds the predetermined threshold torque, and hence interrupt the transmission to the capsule of the rotational driving torque.

13. The unit of claim 12, wherein the predetermined threshold torque is lower than 5 N.cm.

14. The unit of claim 1, wherein:
the junction means comprises a retainer wire housed in a lumen of the catheter and exiting at the distal end of the catheter, and
the retainer wire is fastened to the capsule coupling member, so that an axial traction exerted in proximal direction on the retainer wire pushes the capsule coupling member closer against the tool conjugated coupling member.

15. The unit of claim 1, wherein the tool further comprises a tubular protective sleeve carried by the catheter distal end and defining an inner volume capable of housing, with an axial sliding degree of freedom: at least the proximal region of the capsule tubular body including the capsule coupling member; the tool conjugated coupling member; and the junction means.

* * * * *